United States Patent [19]

Neidermeyer et al.

[11] Patent Number: 5,008,192
[45] Date of Patent: Apr. 16, 1991

[54] ENZYMATIC PROCESS FOR THE PREPARATION OF OPTICALLY ACTIVE CYANOHYDRINS

[75] Inventors: Uwe Neidermeyer, Walberberg; Udo Kragl, Juelich; Maria R. Kula, Hambach-Neiderzier; Christian Wandrey, Juelich; Kyriakos Makrylaleas; Karlheinz Drauz, both of Freigericht, all of Fed. Rep. of Germany

[73] Assignees: Kernforschungsanlage Juelich GmbH, Juelich; Degussa Aktiengesellschaft, Frankfurt am Main, both of Fed. Rep. of Germany

[21] Appl. No.: 303,336

[22] Filed: Jan. 30, 1989

[30] Foreign Application Priority Data

Jan. 29, 1988 [DE] Fed. Rep. of Germany ....... 3802624
Jul. 14, 1988 [DE] Fed. Rep. of Germany ....... 3823864

[51] Int. Cl.$^5$ ............................................. C12P 13/00
[52] U.S. Cl. ..................................... 435/128; 435/280
[58] Field of Search ................................ 435/128, 280

[56] References Cited

FOREIGN PATENT DOCUMENTS 1300111 4/1970 Fed. Rep. of Germany .

OTHER PUBLICATIONS

Effenberger et al.—Chem. Abst., vol. 107 (1987), p. 3690p.
Effenberger et al., Angew. Chem., 95 (No. 1), (1983) p. 50.
Becker et al., J. Am. Chem. Soc., pp. 4299–4300, (1966).
Effenberger et al., Angew. Chem. 99, pp. 491–492, (1987).
Bove et al., J. Biol. Chem., 236, pp. 207–210 (1961).

*Primary Examiner*—Sam Rosen
*Attorney, Agent, or Firm*—Foley & Lardner

[57] ABSTRACT

An enzymatic reaction of aliphatic, aromatic or heteroaromatic aldehydes or ketones with hydrocyanic acid to form the corresponding (R)-cyanohydrins or (S)-cyanohydrins is carried out in an aqueous medium in the presence of (R)-oxynitrilase (4.1.2.10) or oxynitrilase (4.1.2.11) under acid conditions and at temperatures such that the competing chemical reaction and racemization are negligible compared with the enzymatic synthesis. The process is preferably carried out at a pH of $\leq 4.5$ and at reaction temperatures between $-5°$ C. and $+50°$ C. The reaction is preferably carried out continuously, advantageously in an enzyme membrane reactor. Of particular interest is the conversion of aromatic aldehydes into the corresponding optically active cyanohydrins.

27 Claims, No Drawings

ENZYMATIC PROCESS FOR THE PREPARATION OF OPTICALLY ACTIVE CYANOHYDRINS

BACKGROUND OF THE INVENTION

The present invention relates to a process for the preparation of optically active cyanohydrins of high optical purity through enzymatic reactions of oxo compounds with hydrocyanic acid in the presence of oxynitrilase.

Optically active cyanohydrins produced by oxynitrilase catalysed addition of HCN to aldehydes or ketones, e.g., derivatives of m-phenoxybenzaldehyde and substituted analogues, are employed as components for the synthesis of photostable pyrethroids.

They are also used for the synthesis of optically active α-hydroxycarboxylic acids. The latter are in turn employed as feedstuff additives or for obtaining pharmaceutically active compounds, vitamins and liquid crystals.

According to Effenberger et al., Angew. Chem., 95 (No.1), 50 (1983), these optically active α-hydroxycarboxylic acids can advantageously be converted into optically active N-substituted α-amino acids, which are otherwise difficult to prepare.

Optically active cyanohydrins likewise provide easy access to optically active α-amino alcohols and further optically active compounds which can be derived therefrom and are important in the synthesis of biologically active compounds.

German Patent 1,300,111 discloses a process for the preparation of optically active (R)-cyanohydrins in which aldehydes are reacted with hydrocyanic acid in the presence of oxynitrilase. In this known process, the reaction is carried out in an aqueous or aqueous/alcoholic (50 % v/v) reaction medium at a pH of 5.4 (or 4.8 to 5.4; see Becker et al., J. Am. Chem Soc., 1966, 4299), i.e. just below the optimum pH for the enzyme activity, which is between 5.6 and 6. However, the optical purity of the (R)-cyanohydrins produced by this process exhibited some problems.

Effenberger et al., Angew. Chem. 99, 491–2 (1987), investigated the enzymatic formation of cyanohydrins in aqueous/alcoholic systems with variation of the pH, temperature and concentration, with respect to providing optimum suppression of the chemical addition of hydrocyanic acid to the aldehyde group, which accompanies and competes with the enzyme-catalyzed addition and results in racemates. Since it was not possible to produce satisfactory optimization in this way, Effenberger et al. proposed to suppress the chemical reaction by using organic, water-immiscible solvents. In particular, the process was carried out using ethyl acetate and using support-immobilized (R)-oxynitrilase. In this way, products of high optical purity were obtained, but the reaction in an organic medium means a certain technical obstacle, in particular since the activity and stability of the enzyme are reduced in this medium.

A need therefore continues to exist for a method of synthesizing optically active cynohydrins of high optical purity without the disadvantages of the prior art methods.

OBJECTS OF THE INVENTION

One object of the invention is to provide a process for the enzymatic preparation of optically active cyanohydrins which is carried out in aqueous medium and in which, nevertheless, high optical purities can be achieved.

Another object of the invention is to provide a process for producing optically active cyanohydrins which is well suited to continuous operation.

SUMMARY OF THE INVENTION

These and other objects of the invention, which will become more readily apparent upon study of the present disclosure, are achieved by providing a process for the preparation of an optically active cyanohydrin, which comprises the steps of reacting an aliphatic, aromatic or heteroaromatic aldehyde or ketone which could be substituted or unsubstituted with hydrocyanic acid in an aqueous medium, in the presence of (R)-oxynitrilase (4.1.2.10) or (S)-oxynitrilase (4.1.2.11), under acid conditions and at a temperature such that the competing chemical reaction and racemization are negligible compared with the enzymatic synthesis, and recovering resultant cyanohydrin of high optical purity.

DETAILED DESCRIPTION

The process according to the invention, developed for this purpose, is characterized in that (R)-cyanohydrins or (S)-cyanohydrins derived from aliphatic, aromatic or heteroaromatic aldehydes or ketones are prepared by reacting the corresponding oxo compounds with hydrocyanic acid in an aqueous medium in the presence of (R)-oxynitrilase (4.1.2.10) or oxynitrilase (4.1.2.11) under acid conditions and at temperatures such that the competing chemical reaction and racemization are negligible compared with the enzymatic synthesis.

Oxynitrilase (4.1.2.11) originating from Sorghum bicolor has been described, for example, by Bove et al., J. Biol. Chem., 236, 207 (1961). However, its utility for obtaining optically pure (S)-cyanohydrins was hitherto unknown. Hereinafter, this enzyme is denoted (S)-oxynitrilase.

Surprisingly, it has been found that the activity of both enzymes with respect to the synthesis of cyanohydrins, although reduced, is still sufficient at relatively low pH values at which the chemical addition of hydrogen cyanide and production of racemic product can be suppressed. The optimum pH range in each case depends to a certain extent on the substrates employed, with pH values up to a maximum of about 4.5 generally being preferred.

The aqueous medium can contain a maximum of 40%, more preferably no more than 25%, of organic co-solvent. It should be noted, however, that the oxynitrilases only have adequate activity if the pH reduction is also accompanied by a reduction in the co-solvent content. However, since the enzyme activity is considerably reduced by the presence of even small amounts of organic co-solvents (for example ethanol), the process should preferably be carried out in the substantial absence of organic co-solvent.

The chemical reactivity of the carbonyl compound and the affinity of the enzyme therefor determine the extent to which the pH must be reduced as a function of the temperature so that the chemical synthesis of cyanohydrin is negligible compared with the enzymatic synthesis. However, pH values of below 2.8 are not advisable since the oxynitrilases are then deactivated too rapidly.

Working in an aqueous medium makes it possible to use the particular enzyme in dissolved form and considerably simplifies the metered addition. Furthermore, a continuous procedure, in particular in an enzyme membrane reactor (EMR), is thus simple to carry out, and work-up by extraction of the cyanohydrins formed with water immiscible solvents, e.g., methylene chloride, chloroform, 1,2-dichloroethane, ethyl acetate, isopropyl acetate, methyl tert-butyl ether, is possible without difficulties.

In the reaction according to the invention, it will be appreciated that the enzymatic activity and the stability of the enzyme are lower at lower pH, but (R)-oxynitrilase (4.1.2.10) from Prunus amygdalus and (S)-oxynitrilase (4.1.2.11) from Sorghum bicolor are readily obtained and commercially available, which means that it is possible to use increased amounts and that any further supply which may be necessary is possible without difficulty, in particular since the reduction in enzyme stability is not excessively high (for example 8% per day at pH 3.75 and 20° C. for (R)-oxynitrilase).

According to the invention, all carbonyl compounds which are substrates for the oxynitrilases, and for which purely chemical formation of cyanohydrin can be suppressed by reducing the pH to 2.8 can be reacted to produce (R)- or (S)-cyanohydrin in very high optical purity (ee>99%).

The process of the invention includes the formation of cyanohydrins from aliphatic and aromatic aldehydes, the latter including unsubstituted or substituted homoaromatic or heteroaromatic aldehydes. Ketones which can bind to the active site of the oxonitrilase enzymes can also serve as substrates in the present process. The reaction of aromatic aldehydes has been studied particularly carefully, especially the preparation of (R)- and (S)-mandelonitrile and the derivatives thereof starting from optionally substituted benzaldehyde, where an optical purity of greater than 99% ee has been obtained at pH values of 3.25. In addition, the chemical synthesis is suppressed at pH values of 3.75 to an extent such that an optical purity of greater than 98% ee is obtained under otherwise identical conditions.

Carbonyl compounds which are less reactive than benzaldehyde can correspondingly be reacted at higher pH values without loss of enantioselectivity: thus, furfural can be reacted under otherwise identical conditions, but at pH 4.0, to form (R)-cyanohydrin in an optical purity of 99% ee.

Besides varying the pH, one can vary the substrate concentration over a relatively wide range and/or reduce the reaction temperature in order to inhibit the accompanying chemical reaction. Preferably, a reaction temperature of about −5° C. to +50° C. is employed. Thus, the present process provides a certain latitude for favorable reaction conditions.

According to the invention, substrates which can be reacted are, in particular, aliphatic, aromatic and heterocyclic, especially heteroaromatic, aldehydes or ketones in the presence of (R)-oxynitrilase, or aromatic or heteroaromatic aldehydes with (S)-oxynitrilase, with formation of the optically pure (R)- or (S)-enantiomers of the cyanohydrins produced. Cyanohydrins of aromatic aldehydes are of particular interest for use in the area of pharmaceuticals.

The invention is described in greater detail below with reference to certain examples, where Examples 1 to 13 describe the preparation of (R)-enantiomers and Examples 14 to 18 describe the formation of (S)-enantiomers. The examples are provided for illustrative purposes and are not intended to limit the scope of the invention.

EXAMPLE 1

53 mg (0.5 mmol) of benzaldehyde were dissolved in 9.4 ml of 50 mM citrate buffer at pH 3.25, and the temperature of the solution was held at 20° C. 125 μl of aqueous (R)-oxynitrilase solution solution were added thereto. The reaction was monitored polarimetrically ($\lambda$=578 nm). After 30 to 45 minutes, a constant rotation was established, and the reaction was complete. The reaction mixture was then extracted four times with 10 ml of chloroform.

The combined organic phases were dried over sodium sulphate, and the solvent was stripped off on a rotary evaporator. The residue was subsequently washed three times with 10 ml of pentane in each case, and the product was dried in vacuo.

Chemical yield: 61.8 mg (93% of theory).

Optical purity: >99% ee.

The optical purity was determined as the N,O-bis-(pentafluoropropionyl)-2-amino-1-phenylethanol derivative of (R)-mandelonitrile by capillary gas chromatography by the method of Frank et al., J. Chromatogr., 146, 197–206 (1987), on a chiral separating phase (FS-Chirasil-Val, 25 m×0.32 mm).

The derivatization was carried out as follows: 1–2 mg of mandelonitrile were reduced at room temperature for 30 minutes using 250 μl of a 1M diborane solution (in tetrahydrofuran) in chloroform. After the excess diborane had been hydrolysed using a few drops of ethanol and after the solvent had been stripped off, the aminoalcohol obtained was acylated directly at room temperature for 15 minutes using 20 μl of pentafluoropropionic anhydride in methylene chloride. The excess anhydride was finally stripped off on a rotary evaporator and the residue was taken up again in methylene chloride and analyzed by gas chromatography.

EXAMPLE 2

48 mg (0.5 mmol) of furfural were reacted at pH 4.0 in accordance with Example 1. The reaction was complete after about 30 minutes. The (R)-cyanohydrin was isolated as described in Example 1.

Chemical yield: 55.3 mg (90% of theory).

Optical purity: 99% ee.

In order to determine the optical purity, the cyanohydrin was converted into the diastereomeric esters using (R)-$\alpha$-methoxy-$\alpha$-trifluoromethylphenylacetyl chloride by the method of Elliott et al., (J. Org. Chem., 48 2294–2295 (1983), and the diastereomer ratio was determined by capillary gas chromatography (FS-OV 1 10 m×0.32 mm).

EXAMPLE 3

22 mg (0.5 mmol) of acetaldehyde were reacted at pH 3.25 in accordance with Example 1. The reaction was complete after about 90 minutes. The work-up was carried out analogously to example 1.

Chemical yield: 26 mg (73% of theory).

Optical purity: 76% ee.

The optical purity was determined in accordance with Example 1 via N,O-bis-pentafluoropropionyl-amino-2-propanol.

EXAMPLE 4

56 mg (0.5 mmol) of 3-methylcyclohexanone were reacted at pH 4.0 in accordance with Example 1. The reaction was complete after 90 minutes.
Chemical yield: 57 mg (83% of theory).
Optical purity: not determined.

EXAMPLE 5

Continuous production of (R)-mandelonitrile in an enzyme membrane reactor (EMR) was carried out using increased amounts of reactants. The operating conditions of the EMR (corresponds to a continuously operated stirred tank reactor) allow the use of relatively high pH values, corresponding to mild conditions, without loss of optical purity of the product. The continuous production results in more economical utilization of the enzyme since it is separated off by ultrafiltration before the product is worked up.

Thus, 7 g of optically pure (R)-mandelonitrile (ee>99%) were produced in a continuous procedure in a 10 ml EMR in 26 hours.

Operating conditions:
Benzaldehyde: 48 mmol/l
HCN: 180 mmol/l
Citrate buffer: 45 mmol/l pH 3.75
Residence time: 10 min
Enzyme concentration: 0.38 mg/ml
Mean conversion: 84%
Space-time yield: 773 g/(1 . d)
Temperature: 20° C.

EXAMPLE 6

A 0.2 molar isobutyraldehyde solution was reacted at pH =3.6 and T=6° C. in accordance with Example 1. The reaction was complete after 90 minutes.
Chemical yield: 84% of theory.
Optical purity: 96% ee.
$[\alpha]_D^{20} = +16.3°$ (c=5 in $CHCl_3$).

EXAMPLE 7

A 0.25 molar isovaleraldehyde solution was reacted at pH=3.7 and T=7° C. in accordance with Example 1. The reaction was complete after 100 minutes.
Chemical yield: 92% of theory.
Optical purity: 96.8% ee.
$[\alpha]_D^{20} = +24.20°$ (c=5 in $CHCl_3$).

EXAMPLE 8

A 0.25 molar 3-methylmercaptopropionaldehyde solution was reacted at pH=3.3 and T=5° C. in accordance with Example 1. The reaction was complete after 90 minutes.
Chemical yield: 85.5% of theory.
Optical purity: 97.3% ee.
$[\alpha]_D^{20} = +41.0°$ (c=5 in $CHCl_3$).

EXAMPLE 9

A 0.25 molar hydrocinnamaldehyde solution was reacted at pH=4.0 and T=8° C. in accordance with Example 1. The reaction was complete after 80 minutes.
Chemical purity: 93.8% of theory.
Optical yield: 95.1% ee.
$[\alpha]_D^{20} = -6.2°$ (c=5 in $CHCl_3$).

EXAMPLE 10

A 0.25 molar cinnamaldehyde solution was reacted at pH=4.3 and T=8° C. in accordance with Example 1. The reaction was complete after 90 minutes.
Chemical yield: 94% of theory.
Optical purity: 94.7% ee.
$[\alpha]_D^{20} = +23.75°$ (c=5 in $CHCl_3$).

EXAMPLE 11

A 0.25 molar pivalaldehyde solution was reacted at pH=3.3 and T=6° C. in accordance with Example 1. The reaction was complete after 90 minutes.
Chemical yield: 81.4% of theory.
Optical purity: 85% ee.
$[\alpha]_D^{20} = +13.2°$ (c=5 in $CHCl_3$).

EXAMPLE 12

A 0.2 molar butyraldehyde solution was reacted at pH=3.5 and T=7° C. in accordance with Example 1. The reaction was complete after 2 hours.
5 Chemical yield: 83% of theory.
Optical purity: 96.4% ee.
$[\alpha]_D^{20} = +13.6°$ (c=5 in $CHCl_3$).

EXAMPLE 13

A 0.2 molar crotonaldehyde solution was reacted at pH=3.3 and T=5° C. in accordance with Example 1. The reaction was complete after 2 hours.
Chemical yield: 82% of theory.
Optical purity: 97.5% ee.
$[\alpha]_D^{20} = +25.2°$ (c=5 in $CHCl_3$)

EXAMPLE 14

52 mg (0.5 mmol) of para-hydroxybenzaldehyde were dissolved in 9.4 ml of 50 mM citrate buffer of pH 3.75, and the temperature of the solution was held at 20° C. 500 μl of (S)-oxynitrilase solution and 800 μl of 4.2M aqueous HCN solution were added thereto. The reaction was monitored polarimetrically (λ=578 nm). A constant rotation was established after 15 to 30 minutes, and the reaction was complete. The reaction mixture was then extracted four times with 10 ml of diethyl ether. The combined organic phases were dried over sodium sulphate, and the solvent was stripped off on a rotary evaporator. The residue was subsequently washed three times with 10 ml of pentane in each case, and the product was dried in vacuo.
Chemical yield: 64.8 mg (87% if theory).
Optical purity: 99% ee.

The optical purity was determined as the N,O-bis-(pentafluoropropionyl)-2-amino-1-(p-hydroxyphenyl)ethanol derivative of p-hydroxymandelonitrile by capillary gas chromatography by the method of Frank et al. The derivatization was likewise carried out as indicated in Example 1.

The (S)-oxynitrilase solution employed had an activity of 84 U/ ml, where 1 U catalyses the formation of 1 μmol/min of para-hydroxymandelonitrile at 20° C. and pH 3.75.

EXAMPLE 15

61 mg (0.5 mmol) of meta-hydroxybenzaldehyde were reacted at pH 3.25 with 450 μl of 4.2M aqueous HCN solution in accordance with Example 14. The reaction was complete after 30 to 40 minutes. The (S)-3-hydroxymandelonitrile was isolated as described in Example 14.

Chemical yield: 67 mg (90% of theory).
Optical purity: 98% ee.

The optical purity was determined in accordance with Example 1 via the N,O-bis-pentafluoropropionyl-2-amino-1-(m-hydroxyphenyl)ethanol derivative.

EXAMPLE 16

60 mg (0.5 mmol) of meta-methylbenzaldehyde were reacted at pH 3.25 with 475 μl of 4.2M aqueous HCN solution and 500 μl of oxynitrilase solution in accordance with Example 14. The reaction was complete after about 45 minutes. The work-up was carried out analogously to Example 1 to give (S)-3-methylmandelonitrile.

Chemical yield: 59 mg (80% of theory).
Optical purity: 96% ee.

The optical purity was determined in accordance with Example 1 via the N,O-bis-pentafluoropropionyl ester-amide of the corresponding aminoalcohol derivative.

EXAMPLE 17

53 mg (0.5 mmol) of benzaldehyde were reacted at pH 3.25 with 475 μl of 4.2M aqueous HCN solution and 1500 μl of (S)-oxynitrilase solution in accordance with Example 14. The reaction was complete after about 45 minutes. The work-up was carried out analogously to Example 1.

Chemical yield: 48 mg (80% of theory).
Optical purity: 96% ee.

The optical purity was determined in accordance with Example 1 via the N,O-bis-pentafluoropropionyl ester-amide of the corresponding aminoalcohol derivative.

EXAMPLE 18

Continuous production of (S)-para-hydroxymandelonitrile in a stirred tank reactor using immobilized (S)-oxynitrilase was effected. The reaction principle was applied to formation of larger amounts of product in a continuous procedure using (S)-oxynitrilase immobilized on Eupergit ® C (Rohm, Darmstadt).

In a continuous procedure, (S)-para-hydroxymandelonitrile was produced in a 10 ml reactor over the course of 72 hours, at 20° C., at a space-time yield of 57.9 g/(l . d).

Characteristic reaction data:
Para-hydroxybenzaldehyde: 21 mmol/l
HCN: 400 mmol/l
Na-citrate: 45 mmol/l pH 3.75
Residence time: 3960 sec
Catalyst concentration: 0.15 g/ml
Run time: 72 h
Enzyme deactivation: ca. 3 %/d
Reaction conversion: 85%
Enantiomer excess: >98%

The foregoing examples are illustrative, and many variations of reactants and conditions may be effected without departing from the broad scope of the invention, which is defined by the appended claims.

What is claimed is:

1. In a process for the preparation of an optically active (R)-cyanohydrin, which comprises the steps of reacting an aliphatic, aromatic or heteroaromatic aldehyde or ketone with hydrocyanic acid, in the presence of (R)-oxynitrilase and recovering resultant (R)-cyanohydrin, the improvement wherein said (R)-oxynitrilase is (R)-oxynitrilase (4.1.2.10) and the process is carried out in an aqueous medium, under acid conditions and at a temperature range of about −5° C. to +50° C. such that the amount of reactant undergoing a competing chemical reaction and racemization is significantly less than the amount of reactant undergoing the enzymatic synthesis, whereby said recovered resultant (R)-cyanohydrin has an improved optical purity.

2. The process of claim 1, wherein the reaction is carried out at pH≦4.5.

3. The process of claim 2, wherein the pH is 2.8 or higher.

4. The process of claim 1, wherein said reaction is carried out continuously.

5. The process of claim 4, wherein the reaction is carried out in a continuously operated stirred tank reactor with enzyme retention.

6. The process of claim 5, wherein the reaction is carried out in an enzyme membrane reactor.

7. The process of claim 1, wherein the reaction is carried out with an aldehyde.

8. The process of claim 7, wherein said aldehyde is an aliphatic aldehyde.

9. The process of claim 7, wherein said aldehyde is an aromatic aldehyde.

10. The process of claim 9, wherein the reaction pH is from about 3.25 to about 4.0.

11. The process of claim 9, wherein said aldehyde is benzaldehyde or a substituted benzaldehyde.

12. The process of claim 11, wherein the reaction pH is from about 3.25 to about 3.75.

13. The process of claim 1, wherein the resultant (R)-cyanohydrin has an optical purity (enantiomeric excess) of at least 98%.

14. The process of claim 1, wherein said reaction is carried out in the substantial absence of an organic co-solvent.

15. The process of claim 1, wherein said aqueous medium contains up to 40% by volume of a miscible organic co-solvent.

16. In a process for the preparation of an optically active (S)-cyanohydrin, which comprises the steps of reacting an aliphatic, aromatic or heteroaromatic aldehyde or ketone with hydrocyanic acid, in the presence of (S)-oxynitrilase and recovering resultant (S)-cyanohydrin, the improvement wherein said (S)-oxynitrilase is (S)-oxynitrilase (4.1.2.11) and the process is carried out in an aqueous medium, under acid conditions and at a temperature range of about −5° C. to +50° C. such that the amount of reactant undergoing a competing chemical reaction and racemization is significantly less than the amount of reactant undergoing the enzymatic synthesis, whereby said recovered resultant (S)-cyanohydrin has an improved optical purity.

17. The process of claim 16, wherein the reaction is carried out at pH≦4.5.

18. The process of claim 17, wherein the pH is 2.8 or higher.

19. The process of claim 16, wherein said reaction is carried out continuously.

20. The process of claim 19, wherein the reaction is carried out in a continuously operated stirred tank reactor with enzyme retention.

21. The process of claim 16, wherein the reaction is carried out with an aromatic aldehyde.

22. The process of claim 21, wherein the reaction pH is from about 3.25 to about 4.0.

23. The process of claim 21, wherein said aldehyde is benzaldehyde or a substituted benzaldehyde.

24. The process of claim 23, wherein the reaction pH is from about 3.25 to about 3.75.

25. The process of claim 16, wherein the resultant (S)-cyanohydrin has an optical purity (enantiomeric excess) of at least 98%.

26. The process of claim 16, wherein said reaction is carried out in the substantial absence of an organic co-solvent.

27. The process of claim 16, wherein said aqueous medium contains up to 40% by volume of a miscible organic co-solvent.

* * * * *